(12) United States Patent
Damon

(10) Patent No.: US 6,172,081 B1
(45) Date of Patent: Jan. 9, 2001

(54) TETRAHYDROISOQUINOLINE 3-CARBOXAMIDE DERIVATIVES

(75) Inventor: Robert Damon, Randolph, NJ (US)

(73) Assignee: Novartis AG, Basel (CH)

( * ) Notice: Under 35 U.S.C. 154(b), the term of this patent shall be extended for 0 days.

(21) Appl. No.: 09/339,504

(22) Filed: Jun. 24, 1999

(51) Int. Cl.$^7$ ................................................ A61K 31/47
(52) U.S. Cl. .......................................... 514/307; 546/146
(58) Field of Search .............................. 514/307; 546/146

(56) References Cited

U.S. PATENT DOCUMENTS

| | | | |
|---|---|---|---|
| 5,430,023 | 7/1995 | Gesellchen et al. | 514/18 |
| 5,491,164 | 2/1996 | deSolms et al. | 514/423 |
| 5,714,485 | 2/1998 | Lumma et al. | 514/247 |

FOREIGN PATENT DOCUMENTS

| | | |
|---|---|---|
| 1581 09 | 12/1982 | (DE) . |
| 296 075 A5 | 11/1991 | (DE) . |
| 555 824 A1 | 8/1993 | (EP) . |
| WO 90/12005 | 10/1990 | (WO) . |
| WO 91/16339 | 10/1991 | (WO) . |
| WO 93/08259 | 4/1993 | (WO) . |
| WO 95/11689 | 5/1995 | (WO) . |
| WO 95/13069 | 5/1995 | (WO) . |
| WO 95/15309 | 6/1995 | (WO) . |
| WO 95/29190 | 11/1995 | (WO) . |
| WO 95/29691 | 11/1995 | (WO) . |
| WO 95/34538 | 12/1995 | (WO) . |

OTHER PUBLICATIONS

Ashworth, et al., Bioorganic and Medicinal Chemistry Letters, vol. 6 (10), pp. 1163–1166 (1996).
Ashworth, et al., Bioorganic and Medicinal Chemistry Letters, vol. 6 (22), pp. 2745–2748 (1996).
Augustyns, et al., Eur.J.Med.Chem., vol. 32; pp. 301–309 (1997).
Derwent Abstract 84–177689.
Derwent Abstract 95–302548.
Coutts, et al. J.Med.Chem., vol. 39, pp. 2087–2094 (1996).
Deacon, et al. Diabetes, vol. 44, pp. 1126–1131 (1996).
Kaspari, et al. Biochimica et Biophysica., vol. 1293, pp. 147–153 (1996).
Li, et al. Archives of Biochemistry and Biophysics, vol. 323(1), pp. 148–154 (1995).
Li, et al. J. of Neurochemistry, vol. 66, pp. 2105–2112 (1996).
Yamada, et al. Bulletin of the Chemical Society of Japan, vol. 50(7), pp. 1827–1830 (1977).
Yamada, et al. Bulletin of the Chemical Society of Japan, vol. 51(3), pp. 878–883 (1978).

*Primary Examiner*—Amelia Owens
(74) *Attorney, Agent, or Firm*—Joseph J. Borovian

(57) ABSTRACT

Tetrahydroisoquinoline 3-carboxamide derivatives of formula

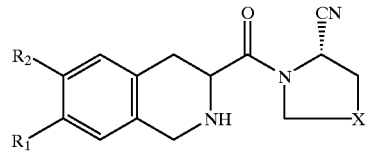

and pharmaceutically acceptable salts thereof wherein:
X is
  (a) $CH_2$;
  (b) S
  (c) O; or
  (d) $C(CH_3)_2$;
$R_1$ and $R_2$ are independently
  (a) hydrogen;
  (b) hydroxy;
  (c) alkyl;
  (d) alkoxy;
  (e) aralkoxy; or
  (f) halogen.

Compounds of formula I inhibit DPP-IV (dipeptidyl-peptidase-IV) activity. They are therefore useful in the treatment of conditions mediated by DPP-IV, such as non-insulin-dependent diabetes mellitus, arthritis, obesity, osteoporosis and further conditions of impaired glucose tolerance.

8 Claims, No Drawings

TETRAHYDROISOQUINOLINE 3-CARBOXAMIDE DERIVATIVES

FIELD OF THE INVENTION

The present invention relates to the area of dipeptidyl peptidase-IV (DPP-IV) inhibition. DPP-IV is a serine protease which cleaves N-terminal dipeptides from a peptide chain containing, preferably, a proline residue in the penultimate position. Although the biological role of DPP-IV in mammalian systems has not been completely established, it is believed to play an important role in neuropeptide metabolism, T-cell activation, attachment of cancer cells to the endothelium and the entry of HIV into lymphoid cells.

More recently, it was discovered that DPP-IV is responsible for inactivating glucagon-like peptide-1 (GLP-1) More particularly, DPP-IV cleaves the amino-terminal His-Ala dipeptide of GLP-1. generating a GLP-1 receptor antagonist, and thereby shortens the physiological response to GLP-1. Since the half-life for DPP-IV cleavage is much shorter than the half-life for removal of GLP-l from circulation, a significant increase in GLP-1 bioactivity (5- to 10-fold) is anticipated from DPP-IV inhibition. Since GLP-1 is a major stimulator of pancreatic insulin secretion and has direct beneficial effects on glucose disposal, DPP-IV inhibition appears to represent an attractive approach for treating non-insulin-dependent diabetes mellitus (NIDDM).

SUMMARY OF THE INVENTION

The instant invention relates to novel tetrahydroisoquinoline 3-carboxamide derivatives of formula I

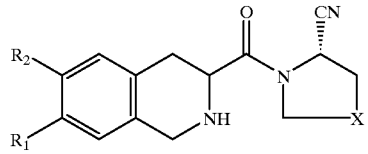

and pharmaceutically acceptable salts thereof. As used in formula I, and throughout the specification, the symbols have the following meanings:

X is
  (a) $CH_2$;
  (b) S;
  (c) O; or
  (d) $C(CH_3)_2$;

$R_1$ and $R_2$ are independently
  (a) hydrogen;
  (b) hydroxy;
  (c) alkyl;
  (d) alkoxy;
  (e) aralkoxy; or
  (f) halogen.

Compounds of formula I are DPP-IV inhibitors which are effective in treating conditions mediated by DPP-IV.

DETAILED DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances either individually or as part of a larger group).

The term "alkyl" refers to optionally substituted straight or branched chain hydrocarbon groups having 1 to 8 carbon atoms, preferably 1 to 5 carbons. Exemplary unsubstituted alkyl groups include methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like. Substituted alkyl groups include said alkyl groups substituted by one or more substituents selected from halogen, alkoxy, cycloalkyl, hydroxy, carboxy, —$CONR_3R_4$, —$NR_3R_4$ (where $R_3$ and $R_4$ are independently hydrogen or alkyl), nitro, cyano or thiol.

The term "alkoxy" refers to any of the above alkyl groups linked to an oxygen atom.

The term "cycloalkyl" refers to saturated cyclic hydrocarbon groups containing 3 to 7 ring carbons with cyclopropyl, cyclopentyl and cyclohexyl being preferred.

The term "halogen" or "halo" refers to chlorine, bromine and fluorine.

The term "aryl" refers to monocyclic or bicyclic aromatic hydrocarbon groups having 6 to 12 carbon atoms in the ring portion, such as phenyl, naphthyl, tetrahydronaphthyl or biphenyl groups, each of which may optionally be substituted by one to four substituents such as alkyl, halo, hydroxy, alkoxy, amino, thiol, nitro, cyano, carboxy and the like.

The term "aralkoxy" refers to an aryl group bonded to an alkoxy group.

The compounds of formula I can exist in free form or in acid addition salt form. Salt forms may be recovered from the free form in known manner and vice-versa. Acid addition salts may e.g. be those of pharmaceutically acceptable organic or inorganic acids. Although the preferred acid addition salts are the trifluoroacetate, the hydrochloric, lactic or acetic acid may also be utilized.

The compounds of the invention may exist in the form of optically active isomers or diastereoisomers and can be separated and recovered by conventional techniques, such as chromatography.

A preferred group of compounds of the invention is the compounds of formula I wherein.

X is $CH_2$; and
  $R_1$ and $R_2$ are independently hydrogen, hydroxy, or alkoxy.

More preferred compounds of the invention are those compounds of formula I wherein
  X is $CH_2$;
  $R_1$ is alkoxy; and
  $R_2$ is hydrogen.

The compounds of formula I may be prepared as illustrated for the compounds of formula I where X is $CH_2$ and one of $R_1$ or $R_2$ is hydroxy or alkoxy according to scheme 1 below:

Scheme 1

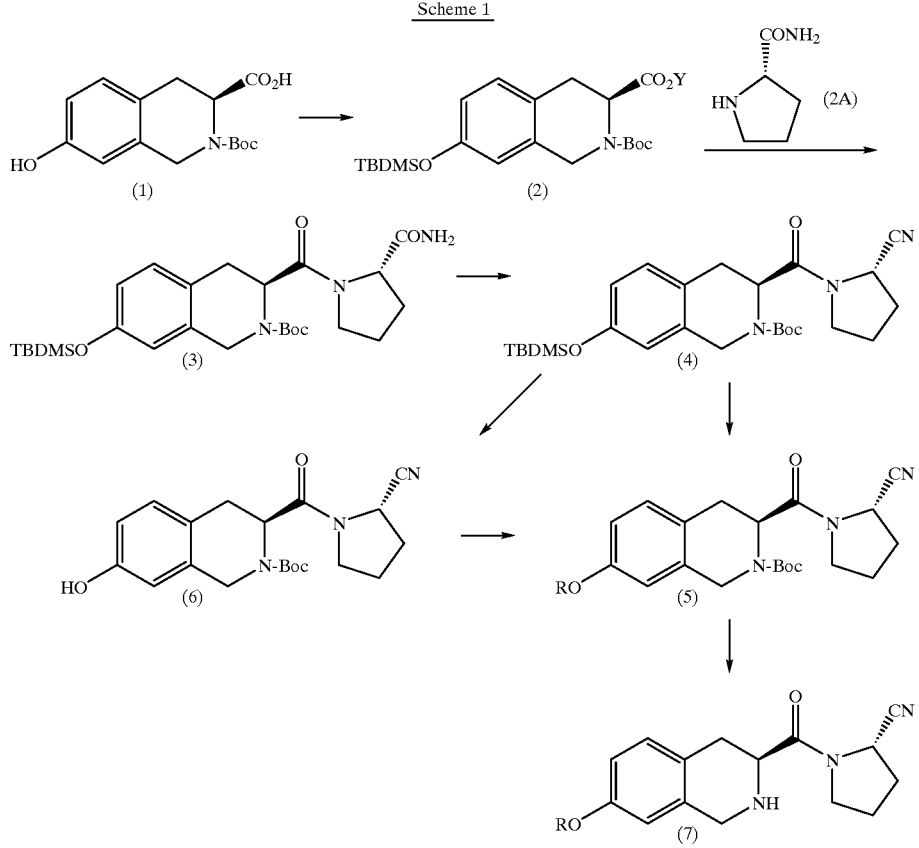

The Boc amino acid derivative (1) is silylated using a silating agent such as t-butyl dimethyl chlorosilane to form compounds of formula (2), where Y is H or a protecting group such as trialkylsilyl, arylalkylsilyl, arylsilyl or t-butyl ester, The silyl derivative (2) is condensed with prolineamide (2A; commercially available) mediated by an activating agent such as EDCI and HOAt in a solvent such as DMF. The resulting amide (3) is dehydrated to the nitrile (4) using a dehydrating agent such as phosphorus oxychloride. The nitrile (4) is then desilylated and alkylated using an alkylating agent such as an alkyl halide of the formula RaX (where Ra is an alkyl or arylalkyl group such as methyl or benzyl and X is a halogen such as iodine, bromine or chlorine) without isolation of the phenol, to form the ether (5). Alternatively, compound (5) can be prepared by alkylating the nitrile (4) with an alcohol subsequent to desilylation via a Mitsunobu-type reaction (via intermediates (6)).

In all cases, the final step is the removal of the Boc group using an acid such as trifluoroacetic acid in an organic solvent such as acetonitrile, preferably in the presence of a scavenger such as 1,3-dimethoxybenzene to give compound (7) which are compounds of formula I where $R_2$ is hydrogen and $R_1$ is alkoxy.

For compounds of formula I where $R_2$ is other than hydroxy condensation with a prolineamide is carried out using the Boc amino acid derivative (1) directly.

The Boc amino acid derivative(1) is commercially available or can be derived using known methods.

Compounds of formula I where X is other than $CH_2$ can be prepared in a similar fashion using the appropriate analog of proline as a starting material. Proline analogs where X=S or O are commercially available and can be used with standard methods of converting the carboxylic acid functionality to a nitrile via the primary amide. In the case where X represents —$C(CH_3)_2$, the requisite proline analog may be prepared as described in either of two literature references: J. Ezquerra, C. Pedregal, A. Rubio, and J. B. Deeter, *Journal of Organic Chemistry* 1994, 59,4327 or F. Soucy, D. Wernic and P. Beaulieu, *JCS Perkin I,* 1991, 2885.

The compounds of the invention may be isolated from the reaction mixture and purified in conventional manner, e.g. by chromatography.

Insofar as its preparation is not particularly described herein, a compound used as starting material is known or may be prepared from known compounds in known manner or analogously to known methods or analogously to methods described in the Examples.

The instant invention also includes pharmaceutical compositions useful in inhibiting DPP-IV comprising a pharmaceutically acceptable carrier or diluent and a therapeutically effective amount of a compound of formula I, or a pharmaceutically acceptable acid addition salt thereof In still another embodiment, the instant invention provides a method of inhibiting DPP-IV comprising administering to a mammal in need of such treatment a therapeutically effective amount of a compound of formula I, or a pharmaceutically acceptable acid addition salt thereof.

In a further embodiment, the instant invention provides a method of treating conditions mediated by DPP-IV inhibition comprising administering to a mammal in need of such treatment a therapeutically effective amount of a compound of formula I above, or a pharmaceutically acceptable acid addition salt thereof.

As indicated above, all of the compounds of formula I, and their corresponding pharmaceutically acceptable acid addition salts, are useful in inhibiting DPP-IV. The ability of the compounds of formula I, and their corresponding pharmaceutically acceptable acid addition salts, to inhibit DPP-IV may be demonstrated employing the Caco-2 DPP-IV Assay which measures the ability of test compounds to inhibit DPP-IV activity from human colonic carcinoma cell extracts. The human colonic carcinoma cell line Caco-2 was obtained from the American Type Culture Collection (ATCC HTB 37). Differentiation of the cells to induce DPP-IV expression was accomplished as described by Reisher, et al. in an article entitled "Increased expression of . . . intestinal cell line Caco-2" in Proc. Natl. Acad. Sci., Vol. 90, pgs. 5757–5761 (1993). Cell extract is prepared from cells solubilized in 10 mM Tris-HCl, 0.15 M NaCl, 0.04 t.i.u. aprotinin, 0.5% nonidet-P40, pH 8.0, which is centrifuged at 35,000 g for 30 min. at 4° C. to remove cell debris. The assay is conducted by adding 20 mg solubilized Caco-2 protein, diluted to a final volume of 125 mL in assay buffer (25 mM Tris-HCl pH 7.4, 140 mM NaCl, 10 mM KCl, 1% bovine serum albumin) to microtiter plate wells. The reaction is initiated by adding 25 mL of 1 mM substrate (H-Alanine-Proline-pNA; pNA is p-nitroaniline). The reaction is run at room temperature for 10 minutes after which time a 19 mL volume of 25% glacial acetic acid is added to stop the reaction. Test compounds are typically added as 30 mL additions and the assay buffer volume is reduced to 95 mL. A standard curve of free p-nitroaniline is generated using 0–500 mM solutions of free pNA in assay buffer. The curve generated is linear and is used for interpolation of substrate consumption (catalytic activity in nmoles substrate cleaved/min). The endpoint is determined by measuring absorbance at 405 nm in a Molecular Devices UV Max microtiter plate reader. The potency of the test compounds as DPP-IV inhibitors, expressed as $IC_{50}$, is calculated from 8-point, dose-response curves using a 4-parameter logistic function.

The following $IC_{50}$s were obtained:

| Compound | Caco-2 DPP-IV ($\mu$M) |
| --- | --- |
| Ex. 1 | 0.0076 |
| Ex. 2 | 0.004 |
| Ex. 3 | 0.014 |
| Ex. 4 | 0.009 |
| Ex. 5 | 0.008 |
| Ex. 6 | >10 |
| Ex. 7 | 0.013 |
| Ex. 8 | 0.01 |
| Ex. 9 | 0.01 |
| Ex. 10 | 0.016 |
| Ex. 11 | 0.01 |

The ability of the compounds of formula I, and their corresponding pharmaceutically acceptable acid addition salts, to inhibit DPP-IV may also be demonstrated by measuring the effects of test compounds on DPP-IV activity in human and rat plasma employing a modified version of the assay described by Kubota, et al. in an article entitled "Involvement of dipeptidylpeptidase IV in an in vivo immune response" in Clin. Exp. Immunol., Vol. 89, pgs. 192–197 (1992). Briefly, five mL of plasma are added to 96-well flat-bottom mictotiter plates (Falcon), followed by the addition of 5 mL of 80 mM $MgCl_2$ in incubation buffer (25 mM HEPES, 140 mM NaCl, 1% RIA-grade BSA, pH 7.8). After a 5 min. incubation at room temperature, the reaction is initiated by the addition of 10 mL of incubation buffer containing 0.1 mM substrate (H-Glycine-Proline-AMC; AMC is 7-amino-4-methylcoumarin). The plates are covered with aluminum foil (or kept in the dark,) and incubated at room temperature for 20 min. After the 20 min. reaction, fluorescence is measured using a CytoFluor 2350 fluorimeter (Excitation 380 nm Emission 460 nm; sensitivity setting 4). Test compounds are typically added as 2 mL additions and the assay buffer volume is reduced to 13 mL. A fluorescence-concentration curve of free AMC is generated using 0–50 mM solutions of AMC in assay buffer. The curve generated is linear and is used for interpolation of substrate consumption (catalytic activity in nmoles substrate cleaved/min). As with the previous assay, the potency of the test compounds as DPP-IV inhibitors, expressed as $IC_{50}$, is calculated from 8-point, dose-response curves using a 4 parameter logistic function.

The following $IC_{50}$s were obtained:

| Compound | human plasma DPP-IV ($\mu$M) | rat plasma DPP-IV ($\mu$M) |
| --- | --- | --- |
| Ex. 1 | 0.041 | 0.79 |
| Ex. 3 | 0.004 | 0.016 |
| Ex. 4 | 0.167 | 1.3 |
| Ex. 5 | 0.049 | 0.315 |
| Ex. 7 | 0.012 | 0.078 |
| Ex. 10 | 0.005 | 0.012 |

In view of their ability to inhibit DPP-IV, the compounds of formula I, and their corresponding pharmaceutically acceptable acid addition salts, are useful in treating conditions mediated by DPP-IV inhibition. Based on the above and findings in the literature, it is expected that the compounds disclosed herein are useful in the treatment of conditions such as non-insulin-dependent diabetes mellitus, arthritis, obesity, allograft transplantation, and calcitonin-osteoporosis. More specifically, for example, the compounds of formula I, and their corresponding pharmaceutically acceptable acid addition salts, improve early insulin response to an oral glucose challenge and, therefore, are useful in treating non-insulin-dependent diabetes mellitus.

The precise dosage of the compounds of formula I, and their corresponding pharmaceutically acceptable acid addition salts, to be employed for treating conditions mediated by DPP-IV inhibition depends upon several factors, including the host, the nature and the severity of the condition being treated, the mode of administration and the particular compound employed. However, in general, conditions mediated by DPP-IV inhibition are effectively treated when a compound of formula I, or a corresponding pharmaceutically acceptable acid addition salt, is administered enterally, e.g., orally, or parenterally, e.g., intravenously, preferably orally, at a daily dosage of 0.002–5, preferably 0.02–2.5 mg/kg body weight or, for most larger primates, a daily dosage of 0.1–250, preferably 1–100 mg. A typical oral dosage unit is 0.01–0.75 mg/kg, one to three times a day.

Usually, a small dose is administered initially and the dosage is gradually increased until the optimal dosage for the host under treatment is determined. The upper limit of dosage is that imposed by side effects and can be determined by trial for the host being treated.

The compounds of formula I, and their corresponding pharmaceutically acceptable acid addition salts, may be combined with one or more pharmaceutically acceptable carriers and, optionally, one or more other conventional pharmaceutical adjuvants and administered enterally, e.g., orally, in the form of tablets, capsules, caplets, etc. or parenterally, e.g., intravenously, in the form of sterile injectable solutions or suspensions. The enteral and parenteral compositions may be prepared by conventional means.

The compounds of formula I, and their corresponding pharmaceutically acceptable acid addition salts, may be formulated into enteral and parenteral pharmaceutical compositions containing an amount of the active substance that is effective for treating conditions mediated by DPP-IV inhibition, such compositions in unit dosage form and such compositions comprising a pharmaceutically acceptable carrier.

The compounds of formula I (including those of each of the subscopes thereof and each of the examples) may be administered in enantiomerically pure form (e.g., ee 98%, preferably 99%) or together with the R enantiomer, e.g., in racemic form. The above dosage ranges are based on the compounds of formula I (excluding the amount of the R enantiomer).

The following examples show representative compounds encompassed by this invention and their synthesis. However, it should be clearly understood that they are for purposes of illustration only.

Abbreviations:
EDCI: 1-Ethyl-3-(3-dimethylaminopropyl)carbodiimide hydrochloride
HOAt: 1-Hydroxy-7-azabenzotriazole
DMF: Dimethylformamide
THF: Tetrahydrofuran
TBAF: Tetrabutylammonium fluoride

EXAMPLE 1

[S-(R*,R*)]-1-(1,2,3,4-tetrahydro-3-isoquinolinyl)carbonyl-2-pyrrolidinecarbonitrile trifluoroacetate

A. [S-(R*,R*)]-3-(2-aminocarbonyl-1-pyrrolidinyl)carbonyl-3,4-dihydro-2(1H) isoquinolinecarboxylic acid 1,1-dimethylethyl ester HOAt (450 mg, 3.6 mmol), EDCI (690 mg, 3.6 mmol) and L-prolinamide (411 mg, 3.6 mmol) were added sequentially to a solution of (S)-3,4-dihydro-2,3(1H)-isoquinolinedicarboxylic acid 2-(1,1-dimethylethyl) ester (1.0 g, 3.6 mmol) in 25 mL of dimethyl formamide. The resulting solution was stirred at room temperature for 20 h. The reaction mixture was diluted with 40 mL of water and extracted with methylene chloride. The organic solution was washed with 2N HCl, 10% aqueous sodium bicarbonate and brine, dried over sodium sulfate, and concentrated under vacuum to give 1.34 g of crude product as a white solid.

B. [S-(R*,R*)]-3-(2-cyano-1-pyrrolidinyl)carbonyl-3,4-dihydro-2(1H)-isoquinolinecarboxylic acid 1,1-dimethylethyl ester Phosphorus oxychloride (1.07 g, 0.65 mL, 6.97 mmol) was added to a solution of the amide (1.0 g, 2.68 mmol) and imidazole (237 mg, 3.48 mmol) in pyridine (22 mL) at room temperature. The reaction (which was exothermic) was stirred at room temperature for 1.25 h, then concentrated under vacuum to provide the crude product as a dark brown mushy solid. Flash chromatography on silica gel using ethyl acetate-hexane (60:40) gave 758 mg of product as a yellowish-white solid. This material was rechromatographed on silica gel using 1:1 ethyl acetate:hexane as the eluent to give 675 mg (71%) of the pure product.

C. [S-(R*,R*)]-1-(1,2,3,4-tetrahydro-3-isoquinolinyl)carbonyl-2-pyrrolidinecarbonitrile trifluoroacetate Trifluoroacetic acid (0.2 mL; 2.6 mmol) was added to a solution of 36 mg (0.1 mmol) of the nitrile in 3 mL of acetonitrile at room temperature. The reaction was stirred 21 h., diluted with toluene (1 mL) and concentrated under vacuum. Addition of toluene and concentration under vacuum was repeated three more times. The white solid residue was partitioned between ethyl acetate and water. The aqueous phase was concentrated under vacuum and toluene was again added and removed under vacuum three more times to give 26 mg (70%) of product as a white solid, m.p. 145–150° C. (dec).. MS: Base peak - 256 (MH+ for free amine). $^1$H NMR (CH$_3$OD; 300 MHz): 7.1–7.4 (m, 4H), 4.85 (m, 1H), 4.6 (dd, 1H), 3.7 (m, 2H), 3.5 (dd, 1H), 3.15 (dd, 1H), 2.1–2.4 (m, 4H). $^{13}$C NMR (CH$_3$OD): 119.2 (CN).

EXAMPLE 2

[S-(R*,R*)]-1-(1,2,3,4-tetrahydro-7-hydroxy-3-isoquinolinyl)carbonyl-2-Pyrrolidinecarbonitrile trifluoroacetate

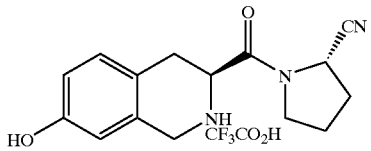

A. (S)-3-(dimethyl)(1,1-dimethylethyl)silyl-ester-7-[(dimethyl)(1,1-dimethylethyl)silyl]oxy-3,4-dihydro-2,3(1H)-Isoquinolinedicarboxylic acid 2-(1,1-dimethylethyl) ester Imidazole (3.1 g; 45.54 mmol) and t-butyldimethylchlorosilane (6.86 g, 45.54 mmol) were added to a solution of (S)-3,4-dihydro-7-hydroxy-2,3(1H)-isoquinolinedicarboxylic acid 2-(1,1-dimethylethyl) ester (6 g, 18.2 mmol) in dimethyl formamide (50 mL) at room temperature. The mixture was stirred at room temperature overnight, then quenched with water and extracted with methyl t-butyl ether. The organic solution was washed with brine, dried (sodium sulfate) and concentrated to give 11.97 g of the title compound as a colorless oil.

B. [S-(R*,R*)]-3-(2-aminocarbonyl-1-pyrrolidinyl)carbonyl-3,4-dihydro-7-[(dimethyl)(1,1-dimethylethyl)silyl]oxy-2(1H)-Isoquinolinecarboxylic acid 1,1-dimethylethyl ester To a solution of the crude title A compound, (S)-3-(dimethyl)(1,1-dimethylethyl)silyl-ester 7-[(dimethyl)(1,1-dimethylethyl)silyl]oxy-3,4-dihydro-2,3(1H)-isoquinolinedicarboxylic acid 2-(1,1-dimethylethyl) ester (9.49 g, 18.22 mmol) in 120 mL of DMF was added EDCI (4.1 g, 21.9 mmol) and HOAt (2.97 g, 21.0 mmol). After stirring for 10 minutes, triethyl amine (2.21 g, 3.05 mL, 21.9 mmol) was added, After an additional 10 minutes, L-prolinamide (2.5 g, 21.9 mmol) was added to the cloudy yellow mixture. The reaction was stirred overnight at room temperature, 1 hour at 50° C., and overnight again at room temperature, and then partitioned between ethyl acetate and water. The ethyl acetate solution was washed with 1N HCl, saturated aq. sodium bicarbonate, and brine, filtered, dried (sodium sulfate), and concentrated to give product as 9.2 g of a white foam. Purification of the crude product by flash chromatography on silica gel using 2% methanol in methylene chloride as the eluent gave 5.7 g of the title compound as a white foam, 91.3% pure by HPLC.

C. [S-(R*,R*)]-3-2-cyano-1-pyrrolidinyl)carbonyl-7-[(dimethyl)(1,1-dimethylethyl)silyl]oxy-3,4-dihydro-2(1H)-Isoquinolinecarboxylic acid 1,1-dimethylethyl ester Phosphorus oxychloride (2 mL, 3.24 g, 21.2 mmol) was added slowly to a solution of the title B compound, [S-(R*,R*)]-3-(2-aminocarbonyl- -pyrrolidinyl)carbonyl-3,4-dihydro-7-[(dimethyl)(1,1-dimethylethyl)silyl]oxy-2(1H)-isoquinolinecarboxylic acid 1,1-dimethylethyl ester (4.1 g. 8.15 mmol) in 40 mL of pyridine at −46° C. Stirring was continued at −46° C. for 1.5 hours after which the temperature was raised to −12° C. over 2 hours. The mixture was allowed to warm to room temperature, diluted with hexane, and concentrated under vacuum to remove the solvents. The residue was chromatographed on silica gel using 20% ethyl acetate/80% hexane as the eluent to give 2.2 g of the title compound as a white foam.

D. [S-(R*,R*)]-3-(2-cyano-1-pyrrolidinyl)carbonyl-3,4-dihydro-7-hydroxy-2(1H)-Isoquinolinecarboxylic acid 1,1-dimethylethyl ester A solution of tetrabutyl ammonium fluoride in THF (2 mL, 2 mmol) was added to a solution of the title C compound, [S-(R*,R*)]-3-(2-cyano-1-pyrrolidinyl)carbonyl-7-[(dimethyl)(1,1-dimethylethyl)silyl]oxy-3,4-dihydro-2(1H)-isoquinolinecarboxylic acid 1,1-dimethylethyl ester (0.8 g, 1.65 mmol) in 2 mL of THF at room temperature. The reaction was stirred for 1 hour after which it was concentrated to remove the solvent. The residue was partitioned between ethyl acetate and aqueous ammonium chloride. The organic solution was dried (sodium sulfate) and concentrated to give product as a white solid. The crude product was chromatographed on silica gel using 5% methanol in methylene chloride as the eluent to give 0.45 g of the title compound as a white solid, m.p. 92–95° C.

E. [S-(R*,R*)]-1-(1,2,3,4-tetrahydro-7-hydroxy-3-isoquinolinyl)carbonyl-2-Pyrrolidinecarbonitrile trifluoroacetate Trifluoroacetic acid (1 mL, 1.48 g, 13 mmol) was added to a solution of the title D compound, [S-(R*,R*)]-3-(2-cyano-1-pyrrolidinyl)carbonyl-3,4-dihydro-7-hydroxy-2(1H)-isoquinolinecarboxylic acid 1,1-dimethylethyl ester (0.3 g, 0.83 mmol) in 5 mL of acetonitrile at room temperature. Stirring was continued for 1.5 hours, after which solvent was removed under vacuum. The residue was triturated with methyl tert-butyl ether to give the title compound as a white solid which was collected by filtration (m.p. 152° C.). MS: 272 (MH+ for free amine). $^1$H NMR (CH$_3$OD; 300 MHz): 7.12 (d, 1H), 6.75 (d, 1H), 6.67 (s, 1H), 4.85 (m, 1H), 4.5 (dd, 1H), 4.42 (s, 2H). 3.7 (m, 2H), 3.4 (dd, 1H), 3.1 (dd, 1H), 2.1–2.4 (m, 4H).

EXAMPLE 3
[S-(R*,R*)]-1-(1,2,3,4-tetrahydro-7-hydroxy-3-isoquinolinyl)carbonyl-2-Pyrrolidinecarbonitrile trifluoroacetate

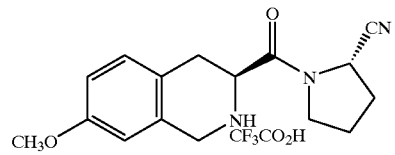

A. [S-(R*,R*)]-3-(2-cyano-1-pyrrolidinyl)carbonyl-3,4-dihydro-7-methoxy-2(1H)-Isoquinolinecarboxylic acid 1,1-dimethylethyl ester.

Methyl iodide (528 mg, 3.72 mmol) was added to a THF solution of the title C compound of Example 2, [S-(R*,R*)]-3-(2-cyano-1-pyrrolidinyl)carbonyl-7-[(dimethyl)(1,1-dimethylethyl)silyl]oxy-3,4-dihydro-2(1H)-isoquinolinecarboxylic acid 1,1-dimethylethyl ester (600 mg, 1.24 mmol) at room temperature. A 1M solution of tetrabutyl ammonium fluoride (1.36 mL, 1.36 mmol) was added slowly during 1 minute. After stirring 2 hours at room temperature, the reaction was quenched with aqueous ammonium chloride. The mixture was then extracted with ethyl acetate. The combined organic extracts were dried (sodium sulfate) and concentrated to give crude product which was purified by flash chromatography on silica gel using a gradient of methanol (1% to 2%) in methylene chloride to give 314 mg of the title compound as a white solid.

B. [S-(R*,R*)]-1-(1,2,3,4-tetrahydro-7-methoxy-3-isoquinolinyl)carbonyl-2-Pyrrolidinecarbonitrile trifluoroacetate.

Trifluoroacetic acid (16.6 mL, 24.56 g, 215.45 mmol) was added to a solution of the title A compound, [S-(R*,R*)]-3-(2-cyano-1-pyrrolidinyl)carbonyl-3,4-dihydro-7-methoxy-2(1H)-isoquinolinecarboxylic acid 1,1-dimethylethyl ester (2.37 g, 6.16 mmol) and 1,3-dimethoxybenzene (4 mL, 4.25 g, 30.78 mmol) in 50 mL of acetonitrile at room temperature. Stirring was continued at room temperature overnight. Excess trifluoroacetic acid was removed under vacuum. Hexane was added and the mixture concentrated under vacuum again, This addition and removal of hexane under vacuum (to remove residual trifluoroacetic acid) was repeated a total of three times. The resulting semi-solid material was triturated with ether and filtered to give 1.96 g. of the title compound, m.p. 150° C. (dec.). $^1$H NMR (DMSO; 250 MHz): 7.15 (d, 1H), 6.9 (d, 1H), 6.8 (s, 1H), 4.85 (dd, 1H), 4.55 (dd, 1H), 4.25 (s, 2H), 3.7 (s, 3H), 3.65 (m, 2H), 3.3 (dd, 1H), 2.85 (dd, 1H), 1.95–2.3 (m, 4H). $^{13}$C NMR: 118.6 (CN). MS: 286 (MH+ for free amine).

EXAMPLE 4
[S-(R*,R*)]-1-(1,2,3,4-tetrahydro-7-phenylmethoxy-3-isoquinolinyl)carbonyl-2-Pyrrolidinecarbonitrile trifluoroacetate

A. [S-(R*,R*)]-3-(2-cyano-1-pyrrolidinyl)carbonyl-3,4-dihydro-7-phenylmethoxy-2(1H)-Isoquinolinecarboxylic acid 1,1-dimethylethyl ester Tetrabutyl ammonium fluoride in THF (2 mL, 2 mmol) was added to a solution of the title C compound of Example 2, [S-(R*,R*)]-3-(2-cyano-1-pyrrolidinyl)carbonyl-7-[(dimethyl)(,1,1-dimethylethyl)silyl]oxy-3,4-dihydro-2(1H)-isoquinolinecarboxylic acid 1,1-dimethylethyl ester (700 mg, 1.4 mmol) and benzyl bromide (431 mg, 2.52 mmol) in THF at room temperature. Stirring was continued for 1.5 hours. Solvent was removed under vacuum and the residue was partitioned between ethyl acetate and aqueous ammonium chloride, The organic solution was dried (sodium sulfate) and concentrated to give the crude product as 410 mg of a white solid, m.p. 58° C.

B. [S-(R*,R*)]-1-(1,2,3,4-tetrahydro-7-phenylmethoxy-3-isoquinolinyl)carbonyl-2-Pyrrolidinecarbonitrile trifluoroacetate.

Trifluoroacetic acid (1 mL, 13 mmol) was added to a solution of the title A compound [S-(R*,R*)]-3-(2-cyano-1- pyrrolidinyl)carbonyl-3,4-dihydro-7-phenylmethoxy-2 (1H)-isoquinolinecarboxylic acid 1,1-dimethylethyl ester (300 mg, 0.65 mmol) in 5 mL of acetonitrile at room temperature. Stirring was continued for 3 hours after which excess solvent was removed under vacuum. Toluene was added and stripped off under vacuum to facilitate the removal of residual trifluoroacetic acid. The residue was triturated with methyl tert-butyl ether to give 213 mg of the title compound as a white solid, m.p. 162° C. $^1$H NMR (DMSO; 300 MHz): 7.3–7.5 (m, 5H), 7.2 (s, 1H), 7.0 (d, 1H), 6.95 (s, 1H), 5.1 (s, 2H), 4.85 (dd, 1H), 4.55 (dd, 1H), 4.3 (s, 2H), 3.65 (m, 2H), 3.35 (dd, 1H), 2.9 (dd, 1H), 1.95–2.35 (m, 4H). MS: 362 (MH$^+$ for free amine).

EXAMPLE 5

[S-(R*,R*)]-1-(1,2,3,4-tetrahydro-7-propoxy-3-isoquinolinyl)carbonyl-2-Pyrrolidinecarbonitrile trifluoroacetate.

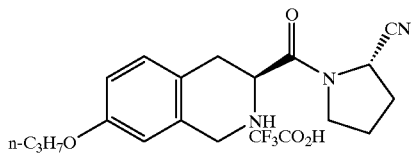

A. [S-(R*,R*)]-3-(2-cyano-1-pyrrolidinyl)carbonyl-3,4-dihydro-7-propoxy-2(1H)-Isoquinolinecarboxylic acid 1,1-dimethylethyl ester Tetrabutyl ammonium fluoride in THF (0.68 mL, 0.68 mmol) was added slowly to a solution of the title C compound of Example 2, [S-(R*,R*)]-3-(2-cyano-1-pyrrolidinyl)carbonyl-7-[(dimethyl)(1,1-dimethylethyl)silyl]oxy-3,4-dihydro-2(1H)-isoquinolinecarboxylic acid 1,1-dimethylethyl ester (300 mg, 0.62 mmol) and 1-iodopropane (72 μL, 126 mg, 0.74 mmol) in 5 mL of THF at room temperature. The reaction was stirred at room temperature for 4 hours and then quenched with ca. 1 mL of saturated aqueous ammonium chloride. Water was added to dissolve the salts and the mixture was extracted with ethyl acetate. The combined organic solution was washed with brine, dried (sodium sulfate) and concentrated under vacuum to give product as 409 mg of a yellow, sticky residue. This material was purified by flash chromatography on silica gel using 1.5% methanol in methylene chloride as the eluent. Product was isolated in 38% yield as a white solid.

B. [S-(R*,R*)]-1-(1,2,3,4-tetrahydro-7-propoxy-3-isoquinolinyl)carbonyl-2-Pyrrolidinecarbonitrile trifluoroacetate.

Trifluoroacetic acid (0.6 mL, 7.8 mmol) was added slowly to a solution of the title A compound, [S-(R*,R*)]-3-(2-cyano-1-pyrrolidinyl)carbonyl-3,4-dihydro-7-propoxy-2 (1H)-isoquinolinecarboxylic acid 1,1-dimethylethyl ester (0.92 mg, 0.22 mmol) in 5 mL of acetonitrile at room temperature. The reaction was stirred for 19 hours after which it was concentrated under vacuum. Additional acetonitrile was added and the mixture was concentrated under vacuum again. Trituration with ether provided the title compound (61 mg, 65%) as a white solid, m.p. 140–153° C. (dec). HPLC analysis indicated the sample was 99.7% pure. $^1$H NMR (CD$_3$OD, 300 MHz): 7.2 (d, 1H), 6.9 (d, 1H), 6.8 (s, 1H), 4.8 (dd, 1H), 4.5 (dd, 1H), 4,4 (s, 1H), 3,8 (t, 2H), 3.65–3.8 (m, 2H), 3.4 (dd, 1H), 3.05 (dd, 1H), 2.1–2.4 (m, 4H), 1.75 (m, 2H), 1.05 (t, 3H). MS: 314 (MH$^+$ of free amine).

EXAMPLE 6

[S-(R*,R*)]-1-[1,2,3,4-tetrahydro-6,7-dimethoxy-3-isoquinolinyl]carbonyl-2-Pyrrolidinecarbonitrile.

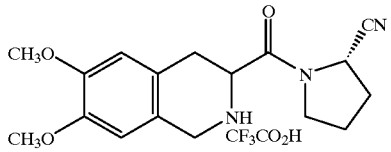

A. 1,2,3,4-tetrahydro-6,7-dimethoxy-3-Isoquinolinecarboxylic acid methyl ester.

Hydrogen chloride gas was bubbled into a suspension of the 3.4-dimethoxy-DL-phenylalanine (4.88 g, 21.7 mmol) in 45 mL of methanol with stirring for 45 minutes. Complete dissolution occurred to give a cloudy yellow solution. The solution was heated to reflux for 1.5 hours, cooled to room temperature, and concentrated under vacuum. The residue was dissolved in hot ethanol (11 mL) to which 8 mL of diethyl ether was added and the mixture was allowed to stand overnight. The resulting solid was collected by filtration and triturated with ether to give 3.91 g (65%) of an amino ester as a slightly off-white powder.

The amino ester from the previous step (551 mg, 2.0 mmol) and paraformaldehyde (60 mg, 2.0 mmol) were combined in formic acid (2.2 mL) and warmed to 44° C. for 24 hours. The mixture was then cooled to room temperature and concentrated under vacuum. The resulting solid residue was treated with 10% aqueous sodium bicarbonate and extracted with methylene chloride. The organic solution was dried (sodium sulfate) and concentrated to give 537 mg of the title compound as an amber oil.

B. 3,4-dihydro-6,7-dimethoxy-2,3(1H)-Isoquinolinedicarboxylic acid 2-(1,1-dimethylethyl) 3-methyl ester.

The amino ester (475 mg. 1.89 mmol) was dissolved in dioxane (7 mL) and 10% aqueous sodium bicarbonate (3.2 mL) followed by water (3 mL) were added. The mixture was stirred at room temperature for 1 hour followed by addition of Boc anhydride (412 mg, 1.89 mmol). Stirring was continued for 2 days after which the mixture was diluted with water and extracted with ethyl acetate. The organic extracts were washed with brine, dried (sodium sulfate) and concentrated to give 576 mg (87%) of the title compound as a viscous yellow oil.

C. 3,4-dihydro-6,7-dimethoxy-2,3(1H)-Isoquinolinedicarboxylic acid 2-(1,1-dimethylethyl) ester Water (64 mg, 0.07 mL. 3.56 mmol) was added to a slurry of potassium t-butoxide (1.44 g, 12.8 mmol) in diethyl ether (25 mL) at 0° C. with stirring. After 5 minutes, the title B compound, 3,4-dihydro-6,7-dimethoxy-2,3(1H)-isoquinolinedicarboxylic acid 2-(1,1-dimethylethyl) 3-methyl ester (570 mg, 1.62 mmol) was added as a solution in 8 mL of ether. Stirring was continued for 45 minutes with warming to 8° C. after which the cooling bath was removed and stirring was continued at room temperature for 45 minutes. The reaction was quenched with 10 mL of saturated aqueous ammonium chloride, diluted with water, and extracted with ether. The aqueous solution was then acidified to pH 5 with 2N hydrochloric acid and extracted with ethyl acetate. The ethyl acetate solution was dried (sodium sulfate) and concentrated to give 554 mg of the title compound as a viscous yellow oil.

D. 3-(2-aminocarbonyl-1-pyrrolidinyl)carbonyl-3,4-dihydro-6,7-dimethoxy-2(1H)-Isoquinolinecarboxylic acid 2-(1,1-dimethylethyl) ester.

To a solution of the title C compound, 3,4-dihydro-6,7-dimethoxy-2,3(1H)-Isoquinolinedicarboxylic acid 2-(1,1-dimethylethyl) ester (465 mg, 1.38 mmol) in dimethyl formamide (14 mL) was added HOAt (189 mg, 1.38 mmol). EDCI (265 mg, 1.38 mmol), and L-prolinamide (157 mg. 1.38 mmol) sequentially. The reaction was stirred at room temperature for 3.5 days and then concentrated under vacuum. The resulting yellow, viscous residue was partitioned between ethyl acetate and water. The organic solution was washed with 2N HCl, 2N sodium hydroxide, and brine, dried (sodium sulfate) and concentrated to give 740 mg of the crude product. This material was combined with 387 mg of similarly prepared material and purified, with separation of diastereomers, by flash chromatography on silica gel using a solvent gradient of methanol (2% to 5%) in methylene chloride as eluent to give diastereomer A, (329 mg; the chromatographically faster moving isomer) and diastereomer B (272 mg) as pale yellow foams.

E. [S-(R*,R*)]-3-(2-cyano-1-pyrrolidinyl)carbonyl-3,4-dihydro-6,7-dimethoxy-2(1H)-Isoquinolinecarboxylic acid 1,1-dimethylethyl ester [Diastereomer A]

Phosphorus oxychloride (215 mg, 0.13 mL, 1.4 mmol) was added to a solution of the title D compound, 3-(2-aminocarbonyl-1-pyrrolidinyl)carbonyl-3,4-dihydro-6,7-dimethoxy-2(1H)-isoquinolinecarboxylic acid 2-(1,1-dimethylethyl) ester (235 mg, 0.54 mmol; diastereomer A) and imidazole (48 mg, 0.7 mmol) in pyridine (5 mL) at −45° C. The reaction was stirred for 1.75 hours, then allowed to stand at 8° C. overnight, after which the mixture was concentrated under vacuum. The residue was purified by flash chromatography on silica gel using 1% methanol in methylene chloride as eluent to give 190 mg of the title compound as a pale yellow solid.

F. [S-(R*,R*)]-1-[1,2,3,4-tetrahydro-6,7-dimethoxy-3-isoquinolinyl]carbonyl-2-Pyrrolidinecarbonitrile.

Trifluoroacetic acid (1.2 mL, 15.6 mmol) was added to a solution of the title E compound, [S-(R*,R*)]-3-(2-cyano-1-pyrrolidinyl)carbonyl-3,4-dihydro-6,7-dimethoxy-2(1H)-isoquinolinecarboxylic acid 1,1-dimethylethyl ester [Diastereomer A] (185 mg, 0.45 mmol) in acetonitrile (9 mL) at room temperature. The resulting solution was stirred at room temperature overnight after which it was concentrated under vacuum. An additional portion of acetonitrile (8 mL) was added and removed under vacuum. The brown, oily residue was triturated with ether and the resulting solid was collected and washed with ether to give 169 mg of the title compound as a brownish yellow solid, approximately 81% pure by HPLC. $^1$H NMR (CD$_3$OD; 300 MHz): 6.85 (s, 1H), 6.82 (s, 1H). 4.85 (m, 1H), 4.55 (dd, 1H), 4.35 (s, 2H), 3.8 (s, 6H), 3.5–3.9 (m, 2H), 3.3 (dd, 1H), 3.0 (dd, 1H), 2.15–2.35 (m, 4H). MS: 316 (base peak, MH$^+$ for free base).

EXAMPLE 7

1-[1,2,3,4-tetrahydro-6,7-dimethoxy-3-isoquinolinyl] carbonyl-2-Pyrrolidinecarbonitrile [Diastereomer B].

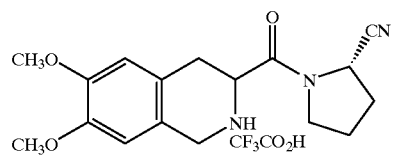

A. 3-(2-cyano-1-pyrrolidinyl)carbonyl-3,4-dihydro-6,7-dimethoxy-2(1H)-Isoquinolinecarboxylic acid 1,1-dimethylethyl ester [Diastereomer B].

Phosphorus oxychloride (239 mg, 0.15 mL, 1.56 mmol) was added to a solution of the title D compound of Example 6, 3-(2-aminocarbonyl-1-pyrrolidinyl)carbonyl-3,4-dihydro-6,7-dimethoxy-2(1H)-isoquinolinecarboxylic acid 2-(1,1-dimethylethyl) ester (259 mg, 0.6 mmol; diastereomer B) and imidazole (53 mg, 0.78 mmol) in pyridine (6 mL) at −45° C. The reaction was stirred for 1.75 hours, then allowed to stand at 8° C. overnight, after which the mixture was concentrated under vacuum. The residue was purified by flash chromatography on silica gel using 2% methanol in methylene chloride as eluent to give 205 mg of the title compound as a yellowish white solid.

B. 1-[1,2,3,4-tetrahydro-6,7-dimethoxy-3-isoquinolinyl] carbonyl-2-Pyrrolidinecarbonitrile [Diastereomer B].

Trifluoroacetic acid (1.2 mL, 15.6 mmol) was added to a solution of the title A compound, 3-(2-cyano-1-pyrrolidinyl) carbonyl-3,4-dihydro-6,7-dimethoxy-2(1H)-isoquinolinecarboxylic acid 1,1-dimethylethyl ester [Diastereomer B] (196 mg, 0.47 mmol) in acetonitrile (9 mL) at room temperature overnight. The mixture was then concentrated under vacuum. The residue was taken up in another portion of acetonitrile (8 mL) and concentrated again under vacuum. The brown oily residue was triturated with ether to form a solid which was collected and washed with ether and dried under vacuum to give 157 mg (78%) of the title compound as a yellow solid, 88% pure by HPLC, m.p. 153–154° C. (dec). $^1$H NMR (CD$_3$OD, 300 MHz): 6.85 (s, 1H), 6.8 (s, 1H), 4.85 (dd, 1H), 4.55 (dd, 1H), 4.35 (2, 2H), 3.8 (s, 6H), 3.6–3.8 (m, 2H), 3.4 (dd, 1H), 3.1 (dd, 1H), 2.1–2.4 (m, 4H). MS: 316 (MH$^+$ for free amine).

EXAMPLE 8

[S-(R*,R*)]-1-[7-(3-diethylamino)propoxy-1,2,3,4-tetrahydro-3-isoquinolinyl]carbonyl-2-Pyrrolidinecarbonitrile

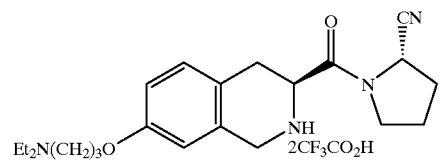

A. [S-(R*,R*)]-3-(2-cyano-1-pyrrolidinyl)carbonyl-3,4-dihydro-7-(3-diethylamino)propoxy-2(1H)-Isoquinolinecarboxylic acid 2-(1,1-dimethylethyl) ester.

Dimethylazodicarboxylate (112 mg, 0.77 mmol) in 2 mL of THF was added to a solution of the title D compound of Example 2, [S-(R*,R*)]-3-(2-cyano-1-pyrrolidinyl) carbonyl-3,4-dihydro-7-hydroxy-2(1H)-Isoquinolinecarboxylic acid 1,1-dimethylethyl ester (220 mg, 0.59 mmol) and triphenylphosphine (202 mg, 0.77 mmol) in THF (12 mL) over 1–2 minutes at room temperature Stirring was continued for 24 hr at room temperature, 24 hours at 47° C., and then an additional 70 hours at reflux. The mixture was cooled to room temperature, concentrated under vacuum, and partitioned between water and ethyl acetate. The organic solution was washed with brine, dried (sodium sulfate) and concentrated to give 560 mg of the crude product as a dark amber oil. The crude product was purified initially using preparative TLC on silica gel using 5% methanol in methylene chloride as eluent to give 184 mg of a dark amber viscous oil, followed by preparative HPLC to give 80 mg of product as a white solid.

B. [S-(R*,R*)]-1-[7-(3-diethylamino)propoxy-1,2,3,4-tetrahydro-3-isoquinolinyl]carbonyl-2-Pyrrolidinecarbonitrile.

Trifluoroacetic acid (0.32 mL, 474 mg, 4.15 mmol) was added to a solution of the title A compound, [S-(R*,R*)]-3-(2-cyano-1-pyrrolidinyl)carbonyl-3,4-dihydro-7-(3-diethylamino)propoxy-2(1H)-isoquinolinecarboxylic acid 2-(1,1-dimethylethyl) ester (60 mg, 0.12 mmol) and 1,3-dimethoxybenzene (83 mg, 0.6 mmol, 79 µL) in acetonitrile ( 3.5 mL) at room temperature. Stirring was continued overnight and the mixture was concentrated under vacuum. An additional two portions (3–4 mL each) of acetonitrile were added and the mixture was again concentrated under vacuum after each portion. The residue was partitioned between ethyl acetate and water. The aqueous solution was lyophilized to give 49 mg (66%) of the title compound as a white powder. HPLC and MS analyses indicated a probable mixture of diastereomers in a 27%:68% ratio. $^1$H NMR (CD$_3$OD, 300 Mhz): 7.2 (d, 1H), 6.95 (d, 1H), 6.85 (s, 1H), 4.85 (dd, 1H), 4.5 (dd, 1H), 4.4 (s, 2H), 4.1 (m, 2H), 3.7 (m, 2H), 3.2–3.5 (m), 3.1 (dd, 1H), 2.1–2.4 (m, 6H), 1.35 (t, 6H). MS: 385 (MH$^+$ for free amine)

EXAMPLE 9

[S-(R*,R*)]-1-[7-[2-(2-ethoxyetoxy)ethoxy]-1,2,3,4-tetrahydro-3-isoquinolinyl]carbonyl-2-Pyrrolidinecarbonitrile trifluoroacetate.

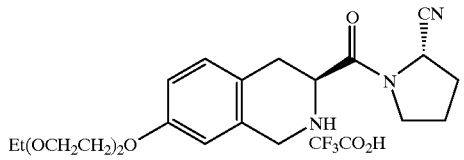

A. [S-(R*,R*)]-3-(2-cyano-1-pyrrolidinyl)carbonyl-3,4-dihydro-7-[2-(2-ethoxyethoxy)ethoxy]-2(1H)-Isoquinolinecarboxylic acid 1,1-dimethylethyl ester.

Tetrabutyl ammonium fluoride (1M in THF; 0.9 mL, 0.9 mmol) was added to a solution of the title C compound of Example 2, [S-(R*,R*)]-3-(2-aminocarbonyl-1-pyrrolidinyl)carbonyl-3,4-dihydro-7-[(dimethyl)(1,1-dimethylethyl)silyl]oxy-2(1H)-isoquinolinecarboxylic acid 1,1-dimethylethyl ester (400 mg, 0.82 mmol) and 1-[2-(ethoxy)ethoxy]ethyl bromide (193 mg, 0.98 mmol) in THF (7 mL) at room temperature. Stirring was continued for 4.5 hours at room temperature, then at reflux for 25 hours, The mixture was cooled to room temperature and quenched with saturated aqueous ammonium chloride, diluted with water, and extracted with ethyl acetate. The combined organic extracts were washed with aq. sodium bisulfate and brine, dried (sodium sulfate) and concentrated to give 399 mg of crude product as a tan, sticky residue. This material was subjected to flash chromatography on silica gel using 2.5% methanol in methylene chloride as eluent to give 170 mg of product which was re-chromatographed on silica gel using 1.5% methanol in methylene chloride as eluent. The title compound was obtained as 104 mg of a pale yellow oil.

B. [S-(R*,R*)]-1-[7-[2-(2-ethoxyethoxy)ethoxy]-1,2,3,4-tetrahydro-3-isoquinolinyl]carbonyl-2-Pyrrolidinecarbonitrile trifluoroacetate.

Trifluoroacetic acid (0.35 mL, 519 mg, 4.55 mmol) was added to a solution of the title A compound, [S-(R*,R*)]-3-(2-cyano-1-pyrrolidinyl)carbonyl-3,4-dihydro-7-[2-(2-ethoxyethoxy)ethoxy]- 2(1H)-isoquinolinecarboxylic acid 1,1-dimethylethyl ester (65 mg, 0.13 mmol) and 1,3-dimethoxybenzene (90 mg, 0.65 mmol) in acetonitrile (3 mL) at room temperature. The mixture was stirred for 24 hours after which it was concentrated under vacuum. Two portions of acetonitrile (3–4 mL each) were added and the mixture was again concentrated under vacuum after each addition. The residue was partitioned between ethyl acetate and water, and the aqueous solution was lyophilized to give 20.4 mg of the title compound (ca. 43%) as a yellow solid, approximately 85% pure by HPLC. $^1$H NMR (CD$_3$OD, 300 Mhz): 7.2 (d, 1H), 6.9 (dd, 1H), 6.8 (s, 1H), 4.85 (dd, 1H), 4.55 (dd, 1H), 4.4 (s, 2H), 4.1 (q, 2H), 3.85 (m, 2H), 3.45–3.8 (m, 8H), 3.4 (dd, 1H), 3.1 (dd, 1H), 2.1–2.4 (m, 4H), 1.1 (t, 3H). MS: 388 (MH$^+$ for free amine).

EXAMPLE 10

[S-(R*,R*)]-[3-(2-cyano-1-pyrrolidinyl)carbonyl-1,2,3,4-tetrahydro-7-isoquinolinyl]oxy-Acetamide.

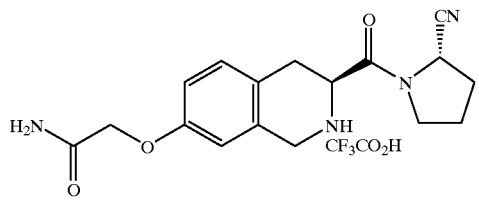

A. [S-(R*,R*)]-3-(2-cyano-1-pyrrolidinyl)carbonyl-3,4-dihydro-7-(2-amino-2-oxoethoxy)-2(1H)-Isoquinolinecarboxylic acid 1,1-dimethylethyl ester Tetrabutyl ammonium fluoride (1M in THF; 1.13 mL, 1.13 mmol) was added to a solution of the title C compound of Example 2, [S-(R*,R*)]-3-(2-aminocarbonyl-1-pyrrolidinyl)carbonyl-3,4-dihydro-7-[(dimethyl)(1,1-dimethylethyl)silyl]oxy-2(1H)-isoquinolinecarboxylic acid 1,1-dimethylethyl ester (500 mg, 1.03 mmol) and iodoacetamide (229 mg, 1.24 mmol) in THF (9 mL) at room temperature. Stirring was continued for 5 hours after which the reaction was quenched with saturated aqueous ammonium chloride and the mixture was partitioned between water and ethyl acetate. The combined organic solution were washed with brine, dried (sodium sulfate) and concentrated under vacuum to give 785 mg of product as a sticky yellow foam. This material was subjected to flash chromatography on silica gel using 2% methanol in methylene chloride as eluent. The collected fractions were combined into two groups, the first (204 mg) consisting mainly (86%) of the un-alkylated phenol, and the latter (402 mg) consisting mainly (93%) of product. This latter fraction was further purified by preparative TLC to give 136 mg of the title compound. 98.5% pure by HPLC.

B. [S-(R*,R*)]-[3-(2-cyano-1-pyrrolidinyl)carbonyl-1,2,3,4-tetrahydro-7-isoquinolinyl]oxy-Acetamide Trifluoroacetic acid (0.8 mL, 1.18 g, 10.4 mmol) was added slowly to a solution of the title A compound, [S-(R*,R*)]-3-(2-cyano-1-pyrrolidinyl)carbonyl-3,4-dihydro-7-(2-amino-2-oxoethoxy)-2(1H)-isoquinolinecarboxylic acid 1,1-dimethylethyl ester (130 mg, 0.3 mmol) and 1,3-dimethoxybenzene (207 mg, 1.5 mmol) in acetonitrile (4 mL) at room temperature. Stirring was continued for 26 hours after which the mixture was concentrated under vacuum at 0° C. Two additional portions of acetonitrile were added, and the mixture was concentrated under vacuum after each additional portion of solvent. The residue was partitioned between water and ethyl acetate, and the aqueous fraction was lyophilized to give 100 mg (75%) of the title compound as a white, fluffy solid. MS: 329 MH$^+$ for free amine). $^1$H NMR (CH$_3$OD; 300 Mhz): 7.25 (d, 1H), 6.95 (d, 1H), 6.85 (s, 1H), 4.85 (dd, 1H), 4.55 (dd, 1H), 4.5 (s, 2H), 4.4 (s, 2H), 3.6–3.8 (m, 2H), 3.4 (dd, 1H), 3.1 (dd, 1H). 2.1–2.45 (m, 4H). $^{13}$C NMR(CH$_3$OD): (CN). HPLC: 97.5% pure.

EXAMPLE 11

[S-(R*,R*)]-[3-(2-cyano-1-pyrrolidinyl)carbonyl-1,2,3,4-tetrahydro-7-isoquinolinyl]oxy-Acetic acid.

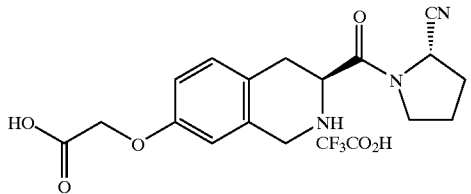

A. [S-(R*,R*)]-3-(2-cyano-1-pyrrolidinyl)carbonyl-3,4-dihydro-7-[2-(1,1-dimethylethoxy)-2-oxoethoxy-2(1H)-Isoquinolinecarboxylic acid 1,1-dimethylethyl ester Tetrabutyl ammonium fluoride (1 M in THF; 0.78 mL, 0.78 mmol) was added dropwise to a solution of the title C compound of Example 2, [S-(R*,R*)]-3-(2-aminocarbonyl-1-pyrrolidinyl)carbonyl-3,4-dihydro-7-[(dimethyl)(1,1-dimethylethyl)silyl]oxy-2(1H)-isoquinolinecarboxylic acid 1,1-dimethylethyl ester (345 mg, 0.71 mmol) and t-butyl bromoacetate (166 mg, 0.85 mmol) in THF (6 mL) at room temperature. Stirring was continued for 4 hours after which the reaction was quenched with saturated aqueous ammonium chloride. Water was added to dissolve the salts, and the mixture was extracted with ethyl acetate. The combined organic solution was washed with brine, dried (sodium sulfate) and concentrated under vacuum to give the crude product as a viscous amber oil. This material was subjected to flash chromatography on silica gel using 1.5% methanol in methylene chloride as the eluent to give 256 mg of material. This material was further purified using preparative TLC on silica gel with 5% methanol in methylene chloride as the eluent to give 152 mg of the title compound.

B. [S-(R*,R*)]-[3-(2-cyano-1-pyrrolidinyl)carbonyl-1,2,3,4-tetrahydro-7-isoquinolinyl]oxy-Acetic acid.

Trifluoroacetic acid (0.84 mL, 1.24 g, 10.9 mmol) was added to a solution of the title A compound, [S-(R*,R*)]-3-(2-cyano-1-pyrrolidinyl)carbonyl-3,4-dihydro-7-[2-(1,1-dimethylethoxy)-2-oxoethoxy-2(1H)-isoquinolinecarboxylic acid 1,1-dimethylethyl ester (150 mg, 0.31 mmol) and 1,3-dimethoxybenzene (214 mg, 1.55 mmol) in acetonitrile (5 mL) at room temperature. Stirring was continued for 3.6 days. The mixture was then concentrated under vacuum at 0° C. Two additional portions of acetonitrile were added, followed in each case by concentration under vacuum. The residue was partitioned between ethyl acetate and water. The aqueous solution was lyophilized to give 83 mg of the title compound. $^1$H NMR (CD$_3$OD, 300 Mhz): 7.25 (d, 1H), 6.95 (dd, 1H), 6.85 (d, 1H), 4.85 (m, 1H), 4.7 (s, 1H), 4.55 (dd, 1H), 4.4 (s, 2H), 3.6–3.8 (m, 2H), 3.4 (dd, 1H), 3.1 (dd, 1H), 2.1–2.4 (m, 4H). MS: 316 (MH$^+$ for free amine).

What is claimed is:

1. A compound of formula I

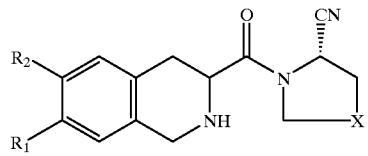

wherein:

X is
(a) CH$_2$;
(b) S;
(c) O; or
(d) C(CH$_3$)$_2$;

R$_1$ and R$_2$ are independently
(a) hydrogen;
(b) hydroxy;
(c) alkyl;
(d) alkoxy;
(e) aralkoxy; or
(f) halogen;
or a pharmaceutically acceptable salt thereof.

2. A compound of claim 1 wherein

X is CH$_2$; and

R$_1$ and R$_2$ are independently hydrogen, hydroxy, or alkoxy.

3. A compound of claim 1 wherein

X is CH$_2$;

R$_1$ is alkoxy; and

R$_2$ is hydrogen.

4. A compound of claim 1 which is:

[S-(R*,R*)]-1-(1,2,3,4-tetrahydro-3-isoquinolinyl) carbonyl-2-pyrrolidinecarbonitrile;

[S-(R*,R*)]-1-(1,2,3,4-tetrahydro-7-hydroxy-3-isoquinolinyl)carbonyl-2-pyrrolidinecarbonitrile;

[S-(R*,R*)]-1-(1,2,3,4-tetrahydro-7-hydroxy-3-isoquinolinyl)carbonyl-2-pyrrolidinecarbonitrile;

[S-(R*,R*)]-1-(1,2,3,4-tetrahydro-7-phenylmethoxy-3-isoquinolinyl)carbonyl-2-pyrrolidinecarbonitrile;

[S-(R*,R*)]-1-(1,2,3,4-tetrahydro-7-propoxy-3-isoquinolinyl)carbonyl-2-pyrrolidinecarbonitrile;

[S-(R*,R*)]-1-[1,2,3,4-tetrahydro-6,7-dimethoxy-3-isoquinolinyl]carbonyl-2-pyrrolidinecarbonitrile;

[S-(R*,R*)]-1-[7-(3-diethylamino)propoxy-1,2,3,4-tetrahydro-3-isoquinolinyl]carbonyl-2-pyrrolidinecarbonitrile;

[S-(R*,R*)]-1-[7-[2-(2-ethoxyethoxy)ethoxy]-1,2,3,4-tetrahydro-3-isoquinolinyl]carbonyl-2-pyrrolidinecarbonitrile;

[S-(R*,R*)]-[3-(2-cyano-1-pyrrolidinyl)carbonyl-1,2,3,4-tetrahydro-7-isoquinolinyl]oxy;

or a pharmaceutically acceptable salt of any of said compounds.

5. A pharmaceutical composition comprising a compound according to claim 1 in free form or in pharmaceutically acceptable acid addition salt form, together with at least one pharmaceutically acceptable carrier or diluent.

6. A method of inhibiting dipeptidyl peptidase-IV comprising administering to a mammal in need of such treatment a therapeutically effective amount of a compound according to claim 1, or a pharmaceutically acceptable acid addition salt thereof.

7. A method of treating conditions mediated by dipeptidyl peptidase-IV inhibition comprising administering to a mammal in need of such treatment a therapeutically effective amount of a compound according to claim 1, or a pharmaceutically acceptable acid addition salt thereof.

8. The method according to claim 7 wherein the condition treated is non-insulin-dependent diabetes mellitus.

* * * * *

UNITED STATES PATENT AND TRADEMARK OFFICE
CERTIFICATE OF CORRECTION

PATENT NO. : 6,172,081 B1
DATED : January 9, 2001
INVENTOR(S) : Robert Damon

Page 1 of 1

It is certified that error appears in the above-identified patent and that said Letters Patent is hereby corrected as shown below:

Column 18,
Insert an "I" to the right of the structural formula.
Line 42, should read: -- [S-(R*,R*)]-1-(1,2,3,4-tetrahydro-7-methoxy-3- --

Signed and Sealed this

First Day of January, 2002

Attest:

Attesting Officer

JAMES E. ROGAN
*Director of the United States Patent and Trademark Office*